US012788962B2

(12) United States Patent
Curran et al.

(10) Patent No.: US 12,788,962 B2
(45) Date of Patent: Nov. 10, 2026

(54) METHOD AND SYSTEM FOR HOLISTICALLY REDUCING PRELOAD AND/OR MODIFYING THE POSITIONING OR CURVATURE OF AN INTERVENTRICULAR SEPTUM

(71) Applicant: ABIOMED, Inc., Danvers, MA (US)

(72) Inventors: Jerald Curran, Danvers, MA (US); Soo Young Kim, Danvers, MA (US)

(73) Assignee: ABIOMED, INC., Danvers, MA (US)

(*) Notice: Subject to any disclaimer, the term of this patent is extended or adjusted under 35 U.S.C. 154(b) by 215 days.

(21) Appl. No.: 18/654,128

(22) Filed: May 3, 2024

(65) Prior Publication Data

US 2024/0366928 A1 Nov. 7, 2024

Related U.S. Application Data

(60) Provisional application No. 63/464,005, filed on May 4, 2023.

(51) Int. Cl.
*A61M 60/178* (2021.01)
*A61B 17/12* (2006.01)
(Continued)

(52) U.S. Cl.
CPC ..... *A61M 60/178* (2021.01); *A61B 17/12122* (2013.01); *A61M 60/13* (2021.01);
(Continued)

(58) Field of Classification Search
CPC .......... A61B 17/12122; A61M 60/178; A61M 60/13; A61M 60/135; A61M 60/237;
(Continued)

(56) References Cited

U.S. PATENT DOCUMENTS

| | | | | |
|---|---|---|---|---|
| 2021/0077792 | A1* | 3/2021 | Kapur | A61B 5/0215 |
| 2021/0177425 | A1 | 6/2021 | Kapur et al. | |
| 2021/0260358 | A1* | 8/2021 | Korakianitis | A61M 60/419 |

FOREIGN PATENT DOCUMENTS

| | | | |
|---|---|---|---|
| WO | 2017031068 | A1 | 2/2017 |
| WO | 2017081561 | A1 | 5/2017 |
| WO | 2019083989 | A1 | 5/2019 |

OTHER PUBLICATIONS

International Search Report and Written Opinion for corresponding PCT Application No. PCT/US2024/027609, dated Oct. 28, 2024.

* cited by examiner

*Primary Examiner* — Michael J Carey
(74) *Attorney, Agent, or Firm* — MEAGHER EMANUEL LAKS GOLDBERG & LIAO, LLP

(57) ABSTRACT

A method for providing a therapeutic treatment to reduce preload may be provided. The method may include placing a ventricular assist device (VAD) at least partially within either the left or right ventricle of a patient, and placing a catheter-based device comprising an adjustable flow restricting element (FRE) such that the FRE is disposed within a superior vena cava (SVC) of the patient. The method may include receiving information from the VAD and/or the catheter-based FRE device, determining a first determined value based on the information, and controlling at least one performance parameter of the VAD and/or the catheter-based device based on the first determined value.

19 Claims, 5 Drawing Sheets

(51) Int. Cl.

| | |
|---|---|
| ***A61M 60/13*** | (2021.01) |
| ***A61M 60/135*** | (2021.01) |
| ***A61M 60/237*** | (2021.01) |
| ***A61M 60/295*** | (2021.01) |
| ***A61M 60/515*** | (2021.01) |
| ***A61M 60/531*** | (2021.01) |
| ***A61M 60/546*** | (2021.01) |
| ***A61M 60/861*** | (2021.01) |

(52) U.S. Cl.
CPC ........ *A61M 60/135* (2021.01); *A61M 60/237* (2021.01); *A61M 60/295* (2021.01); *A61M 60/515* (2021.01); *A61M 60/531* (2021.01); *A61M 60/546* (2021.01); *A61M 60/861* (2021.01)

(58) Field of Classification Search
CPC .............. A61M 60/295; A61M 60/515; A61M 60/531; A61M 60/546; A61M 60/861
USPC ............................................................ 600/16
See application file for complete search history.

METHOD AND SYSTEM FOR HOLISTICALLY REDUCING PRELOAD AND/OR MODIFYING THE POSITIONING OR CURVATURE OF AN INTERVENTRICULAR SEPTUM

TECHNICAL FIELD

The present application claims priority to U.S. Provisional Patent Application No. 63/464,005, filed May 4, 2023, the contents of which are incorporated by reference herein in its entirety.

TECHNICAL FIELD

The disclosure relates to methods and systems for providing improved treatment of cardiac-related issues.

BACKGROUND

Blood pump assemblies, such as intracardiac or intravascular blood pumps may be introduced in the heart to deliver blood from the heart into an artery. Such mechanical circulatory support devices are often introduced to support the function of the heart after a patient suffers a cardiac episode. One such class of devices is the set of devices known as the “Impella” heart pump. Some blood pump assemblies may be introduced percutaneously through the vascular system during a cardiac procedure. Specifically, blood pump assemblies can be inserted via a catheterization procedure through the femoral artery or the axillary/subclavian artery, into the ascending aorta, across the valve and into the left ventricle. The inserted blood pump assembly may be configured to pull blood from the left ventricle of the heart through a cannula and expels the blood into the aorta. A blood pump assembly may also be configured to pull blood from the inferior vena cava and to expel blood into the pulmonary artery.

Systems and methods for treating conditions such as heart failure and/or pulmonary hypertension may include at least partially occluding flow through the superior vena cava for an interval spanning multiple cardiac cycles. In some instances, a catheter with an occlusion device may be provided with a controller that actuates a drive mechanism to provide at least partial occlusion of the patient’s superior vena cava, which may reduce cardiac filling pressures and may induce a favorable shift in the patient’s Frank-Starling curve towards healthy heart functionality and improved cardiac performance.

BRIEF SUMMARY

In various aspects, a method for therapeutically reducing preload may be provided. The method may include providing a plurality of devices, including a ventricular assist device (VAD) and a catheter-based device comprising an adjustable flow restricting element (FRE). The method may include placing the VAD at least partially within either the left or right ventricle of a patient, and placing the catheter-based device such that the FRE may be disposed within a superior vena cava (SVC) of the patient. The method may include receiving information from at least a first device of the plurality of devices. The method may include determining a first determined value based on the information. The method may include controlling at least one performance parameter of at least a second device of the plurality of devices based on the first determined value.

The information may be from both the VAD and the catheter-based device. In some embodiments, the information may be from the VAD and the at least one performance parameter that is controlled may be of the catheter-based device. In some embodiments, the information may be from the VAD and the at least one performance parameter that is controlled may be of both the VAD and the catheter-based device. In some embodiments, the information may be from the catheter-based device and the at least one performance parameter that is controlled may be of the VAD. In some embodiments, the information may be from the catheter-based device and the at least one performance parameter that is controlled may be of both the VAD and the catheter-based device.

The information may be received by a single controller. The single controller may be configured to control both the VAD and the catheter-based device. In some embodiments, any information from the VAD may be received by a first controller, any information from the catheter-based device may be received by a second controller, and the first controller and second controller may be operably communicating with each other.

The information may include left ventricular end diastolic pressure (LVEDP), right ventricular end diastolic pressure (RVEDP), left atrium pressure (LAP), right atrium pressure (RAP), a differential pressure, left ventricle systolic pressure, right ventricle systolic pressure, an arterial pressure, jugular vein pressure (JVP), motor current, an integrated ECG signal, or a combination thereof.

At least one performance parameter may be a rotational speed of a motor of the VAD. In some embodiments, the rotational speed may be increased. In some embodiments, the rotational speed may be decreased. In some embodiments, a limit may be placed on the rotational speed.

At least one performance parameter may be a duty cycle of the FRE. In some embodiments, the duty cycle may be increased. In some embodiments, the duty cycle may be decreased. In some embodiments, the duty cycle may be paused.

The method may include displaying at least one right and left sided hemodynamic metric based on information from the VAD and the catheter-based device. The method may include determining an unloading status of one or more ventricles. The method may include automatically iteratively performing the receiving, determining, and controlling steps of the method to achieve an operational state wherein the unloading status may be a maximally unloaded state that does not compromise patient safety.

In various aspects, a method for modifying the positioning or curvature of an interventricular septum of a patient may be provided. The method may include placing a VAD at least partially within either the left or right ventricle of a patient, and placing a catheter-based device comprising an adjustable flow restricting element (FRE) such that the FRE may be disposed within a superior vena cava (SVC) of the patient. The method may include receiving first information from the VAD and/or the catheter-based device. The method may include determining a first value representative of a first positioning or curvature of the interventricular septum based on the first information. The method may include receiving second information from the VAD and/or the catheter-based device. The method may include determining a second value representative of a second positioning or curvature of the interventricular septum based on the second information. The method may include adjusting at least one performance parameter of the VAD and/or the catheter-based device based on a difference between the first value and the second value, or if the second value exceeds a predetermined threshold.

The information may be from both the VAD and the catheter-based device. In some embodiments, the information may be from the VAD and the at least one performance parameter that is controlled may be of the catheter-based device. In some embodiments, the information may be from the VAD and the at least one performance parameter that is controlled may be of both the VAD and the catheter-based device. In some embodiments, the information may be from the catheter-based device and the at least one performance parameter that is controlled may be of the VAD. In some embodiments, the information may be from the catheter-based device and the at least one performance parameter that is controlled may be of both the VAD and the catheter-based device.

The information may be received by a single controller. The single controller may be configured to control both the VAD and the catheter-based device. In some embodiments, any information from the VAD may be received by a first controller, any information from the catheter-based device may be received by a second controller, and the first controller and second controller may be operably communicating with each other.

The first information may include left ventricular end diastolic pressure (LVEDP), right ventricular end diastolic pressure (RVEDP), left atrium pressure (LAP), right atrium pressure (RAP), a differential pressure, left ventricle systolic pressure, right ventricle systolic pressure, an arterial pressure, jugular vein pressure (JVP), motor current, an integrated ECG signal, or a combination thereof.

The first information may be a value representative of a pressure, distance, or a motor current (such as a motor current of the VAD or the catheter-based FRE device). The distance may be a distance between a sensor on the VAD or the catheter-based device and at least a portion of the intraventricular septum. The pressure may include pressures in right-sided cardiac chambers (e.g., right atrium and/or right ventricle), pressures in left-sided cardiac chambers (e.g., left atrium and/or left ventricle), pressures in the great vessels of the heart, or a combination.

At least one performance parameter may be a rotational speed of a motor of the VAD. In some embodiments, the rotational speed may be increased. In some embodiments, the rotational speed may be decreased. In some embodiments, a limit may be placed on the rotational speed.

At least one performance parameter may be a duty cycle of the FRE. In some embodiments, the duty cycle may be increased. In some embodiments, the duty cycle may be decreased. In some embodiments, the duty cycle may be paused.

The method may include displaying at least one right and left sided hemodynamic metric based on information from the VAD and the catheter-based device.

The method may include automatically iteratively performing several steps. Such steps may include receiving third information from the VAD and/or the catheter-based device. The steps may include determining a third value representative of a third positioning or curvature of the interventricular septum based on the third information. The method may include adjusting at least one performance parameter of the VAD and/or the catheter-based device based on a difference between the third value and one or more previously determined values, or if the third value exceeds a predetermined threshold.

In various aspects a system may be provided for, e.g., providing a therapeutic treatment to reduce preload, and/or optimizing or improving the degree of unloading. The system may include a plurality of devices, that may include a VAD configured to be disposed at least partially in either left or right ventricle, and a catheter-based device comprising an adjustable flow restricting element (FRE), the FRE configured to be disposed within a superior vena cava (SVC) of a patient. The system may include one or more controllers, each controller comprising one or more processors and a non-transitory computer-readable storage media containing instructions that, when executed by the controller, causes the one or more controllers to, individually or in combination, perform several steps. The steps may include receiving information from at least a first device of the plurality of devices. The steps may include determining a first determined value based on the information. The steps may include controlling at least one performance parameter of at least a second device of the plurality of devices based on the first determined value.

The one or more controllers may include a single controller. The one or more controllers may include a first controller operably coupled to the VAD, and a second controller operably coupled to the catheter-based device. The VAD and/or the catheter-based device may include one or more pressure sensors.

In various aspects, a system may be provided, e.g., for modifying the positioning of an interventricular septum of a patient. The system may include a plurality of devices, that may include a VAD configured to be disposed at least partially in either left or right ventricle, and a catheter-based device comprising an adjustable flow restricting element (FRE), the FRE configured to be disposed within a superior vena cava (SVC) of a patient. The system may include one or more controllers, each controller comprising one or more processors and a non-transitory computer-readable storage media (e.g., a storage device) containing instructions that, when executed by the controller, causes the one or more controllers to, individually or in combination, perform several steps. The steps may include receiving first information from the VAD and/or the catheter-based device. The steps may include determining a first value representative of a first positioning of the interventricular septum based on the first information. The steps may include receiving second information from the VAD and/or the catheter-based device. The steps may include determining a second value representative of a second positioning of the interventricular septum based on the second information. The steps may include adjust at least one performance parameter of the VAD and/or the catheter-based device based on a difference between the first value and the second value, or if the second value exceeds a predetermined threshold.

The one or more controllers may include a single controller. The one or more controllers may include a first controller operably coupled to the VAD, and a second controller operably coupled to the catheter-based device. The VAD and/or the catheter-based device may include one or more pressure sensors. The VAD and/or the catheter-based device may include one or more optical sensors. At least one of the one or more optical sensors may be configured to determine a distance. The VAD and/or the catheter-based device may include one or more pressure sensors.

BRIEF DESCRIPTION OF DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
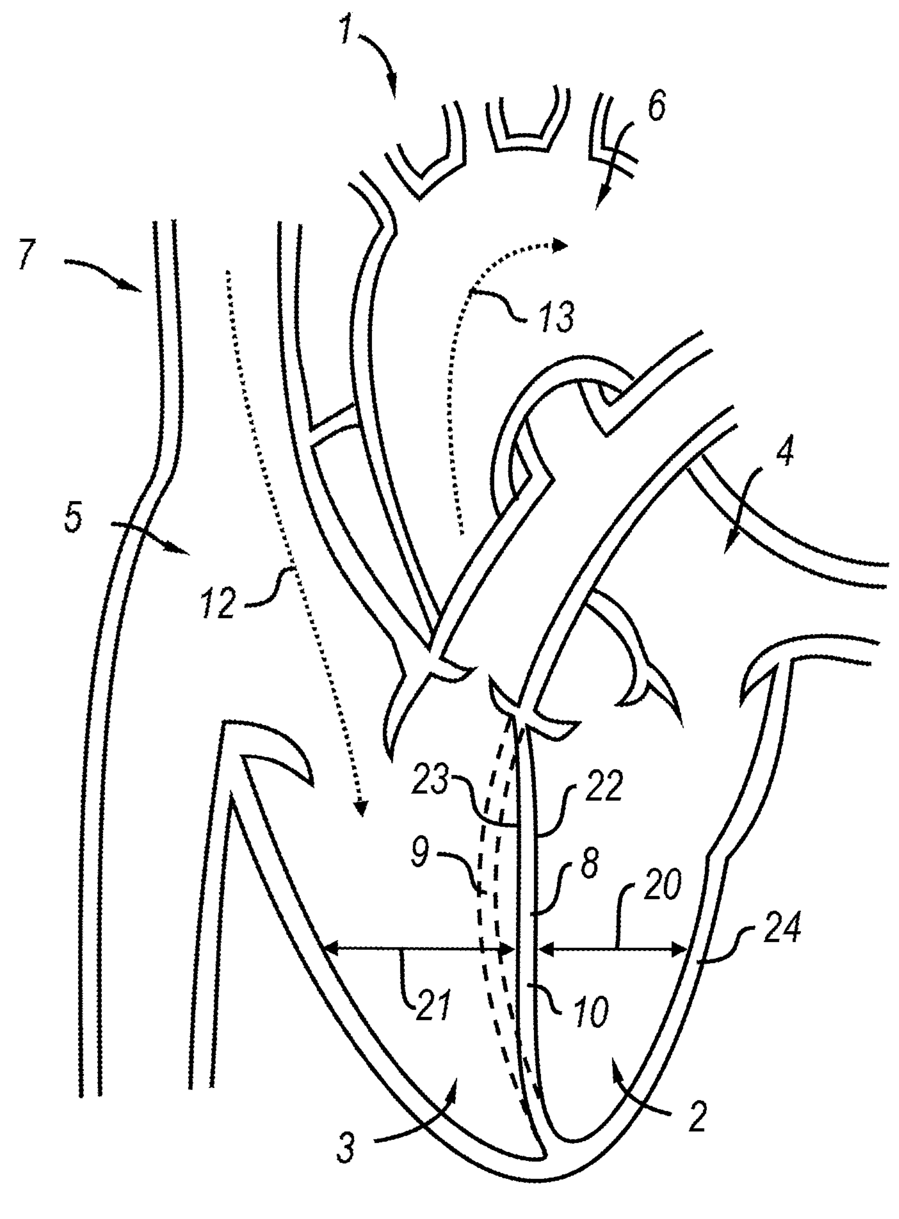
FIG. 1 is an illustration of a heart according to one embodiment.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for illustrative purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the invention may also be applicable to various other technical areas or embodiments.

If the pumping function of a patient's heart is insufficient despite other medical treatments, the circulatory system can be assisted by a ventricular assist device (VAD). For example, in some embodiments, a percutaneous blood pump may be inserted into the patient's heart to assist the heart in pumping blood. In some cases, a flow-restricting device (which may include, e.g., an inflatable balloon) may be additionally installed into the patient's superior vena cava (SVC) to assist in regulating venous blood return to the heart By adjusting the flow-restrictive device, the amount of blood flowing back to the heart can be controlled.

However, the inventors have recognized that controlling such combined treatments may be challenging, as the various performance parameters controlling the devices may counteract each other. Accordingly, embodiments disclosed herein include using a holistic approach to controlling the process provides improved results. For example, in some embodiments, use of the ventricular assist device and the flow-restrictive device may be used as preload reduction therapy. For example, as described herein, the VAD and flow-restrictive devices can be controlled to mechanically regulate preload. In some embodiments, measurements from one and/or both of the devices can be used to mechanically regulate preload. In still further embodiments, the devices may be used to address a septal shift effect, as described herein.

Referring to FIG. 1, a heart (1) can be seen. As seen, blood (12) returning from the superior vena cava (7) to the heart passes through the right atrium (5) and into the right ventricle (3) before being sent to the lungs. Blood returning from the lungs enters the left atrium (4), then the left ventricle (2), before blood (13) leaves the heart and passes into the aortic arch (6).

Cardiac issues may result in the volume of space defined by the left or right ventricle to change, shifting a position of the interventricular septum (8) to reduce the volume in either the left or right ventricle. For example, in FIG. 1, if pressure in the right ventricle (3) increases, the walls may experience a high stress, and the interventricular septum may shift from an original position (9) to a new position (10).

In some embodiments, the positioning and/or curvature of the interventricular septum may define a ratio of the volume of the left ventricle relative to the combined volume of the left and right ventricles. For example, as the intraventricular septum bends or flexes towards the left ventricle (i.e., moves from position (9) to new position (10)), the ratio of the volume of the left ventricle to the combined volume of both ventricles becomes smaller. In some embodiments, the curvature of the interventricular septum may be determined or estimated as a function of distances and/or volumes of the ventricles.

In some embodiments, a width (20) of the left ventricle and a width (21) of the right ventricle may vary with respect to the positioning of the intraventricular septum. The width (20) can be defined as a distance between a surface (22) of the intraventricular septum defining the left ventricle (2) and an external wall (24). Similarly, width (21) can be defined as a distance between a surface (23) of the intraventricular septum defining the right ventricle (3) and an external wall (24). As the positioning of the septum changes, the widths (20, 22) will vary.

In various aspects, as the pressure in the right ventricle increases relative to the pressure in the left ventricle, the septum's position will shift to the left (i.e., reducing the volume of the left ventricle and increasing volume of the right ventricle). Similarly, as the pressure in the left ventricle increases relative to the pressure in the right ventricle, the septum's position will shift to the right (i.e., reducing the volume of the right ventricle and increasing volume of the left ventricle).

Figure 2:
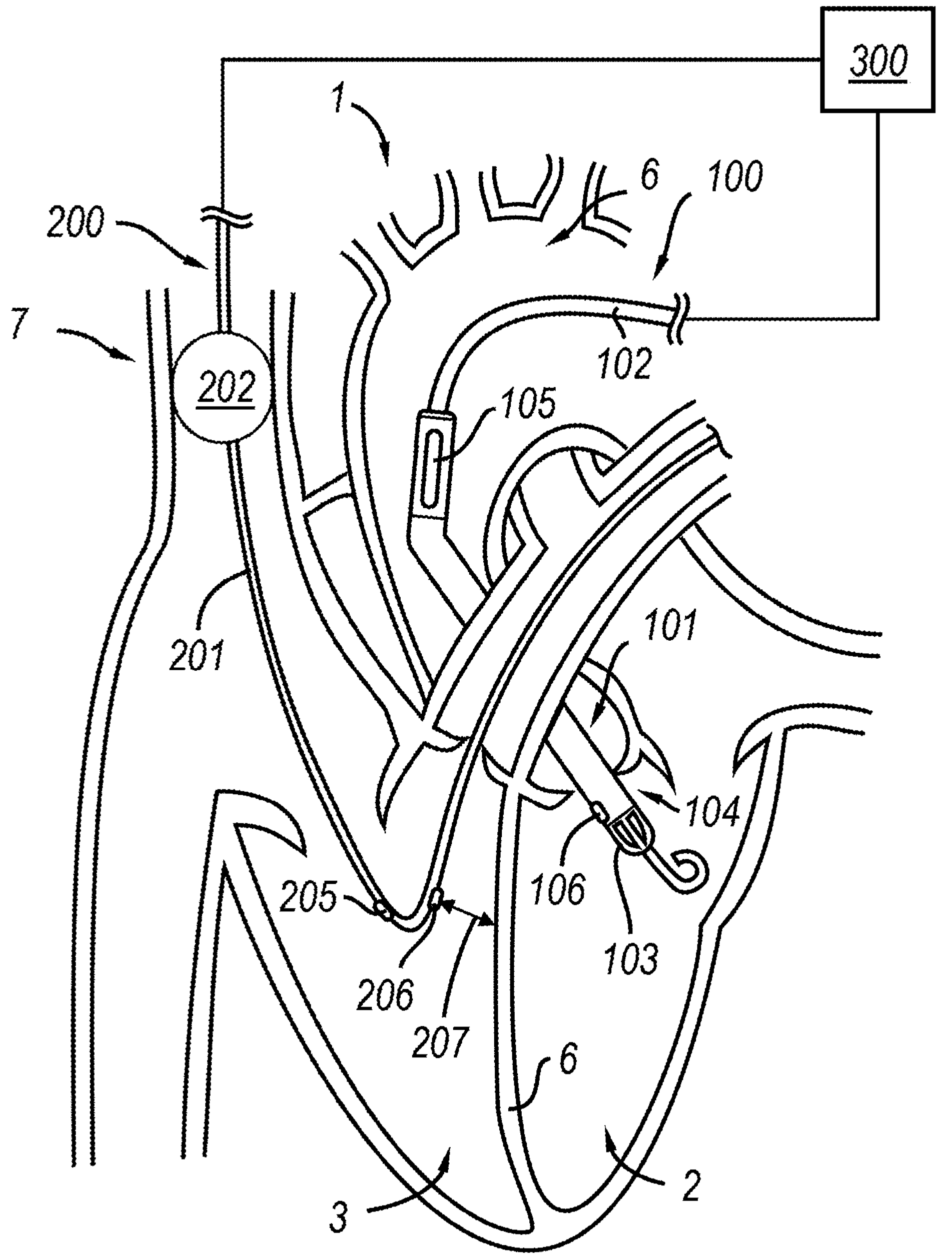
FIG. 2 is an illustration of a heart with two medical devices in place, and a single controller.

Various systems and method may be provided. Referring to FIG. 2, a plurality of devices may be introduced into the patient's vasculature (e.g., the patient's heart), including a ventricular assist device (VAD) (100), such as a percutaneous heart pump, and a catheter-based device (200) comprising an adjustable flow restricting element (FRE) (202) (also referred to herein as a catheter-based FRE device)

As shown in this view, the VAD may include a catheter (102) operably coupled, at a proximal end, to a controller (300). The VAD may include a pump section (101) coupled to a distal end of the catheter. The pump section may include a rotor section (104) that may include a rotor (not shown) configured to cause blood to flow into the blood inlet (103) (which may be positioned, e.g., within the left ventricle or right ventricle), past the rotor, and out through a blood outlet (105) (which may be positioned, e.g., in the aortic arch). By adjusting various operating parameters (such as rotor speed), the amount of blood being transported from one portion of the body to another can be controlled. As will be appreciated, although shown as being positioned in the left heart, in other embodiments, the VAD may be inserted in the right heart to assist with blood flow.

In some embodiments, the FRE (202) of the catheter-based device (200) may be operably coupled to a catheter (201), such that the FRE may be disposed within the superior vena cava 7. The FRE typically has a fully expanded configuration (blocking flow) and a fully collapsed configuration (allowing flow), and may have one or more intermediate configurations. By controlling the degree that the FRE may be expanded, the amount of blood flowing into the right ventricle may be at least partially controlled. The FRE may be also typically on a duty cycle—that is, a first predetermined amount of time may be spent in a first configuration (such as a fully expanded configuration), then the FRE may be switched to a second configuration (such as a fully collapsed configuration) for a second predetermined amount of time. The first and second predetermined amounts of time may be the same (e.g., 1 second expanded, 1 second collapsed), or may be different (e.g., 1 second expanded, 2 seconds collapsed). In some embodiments, the duty cycle may be configured such that the FRE may be in an expanded configuration longer than a collapsed configuration. In some embodiments, the duty cycle may be configured such that the FRE may be in a collapsed configuration longer than an expanded configuration. The proximal end of the catheter-based device may be operably coupled to the controller (300).

Figure 3:
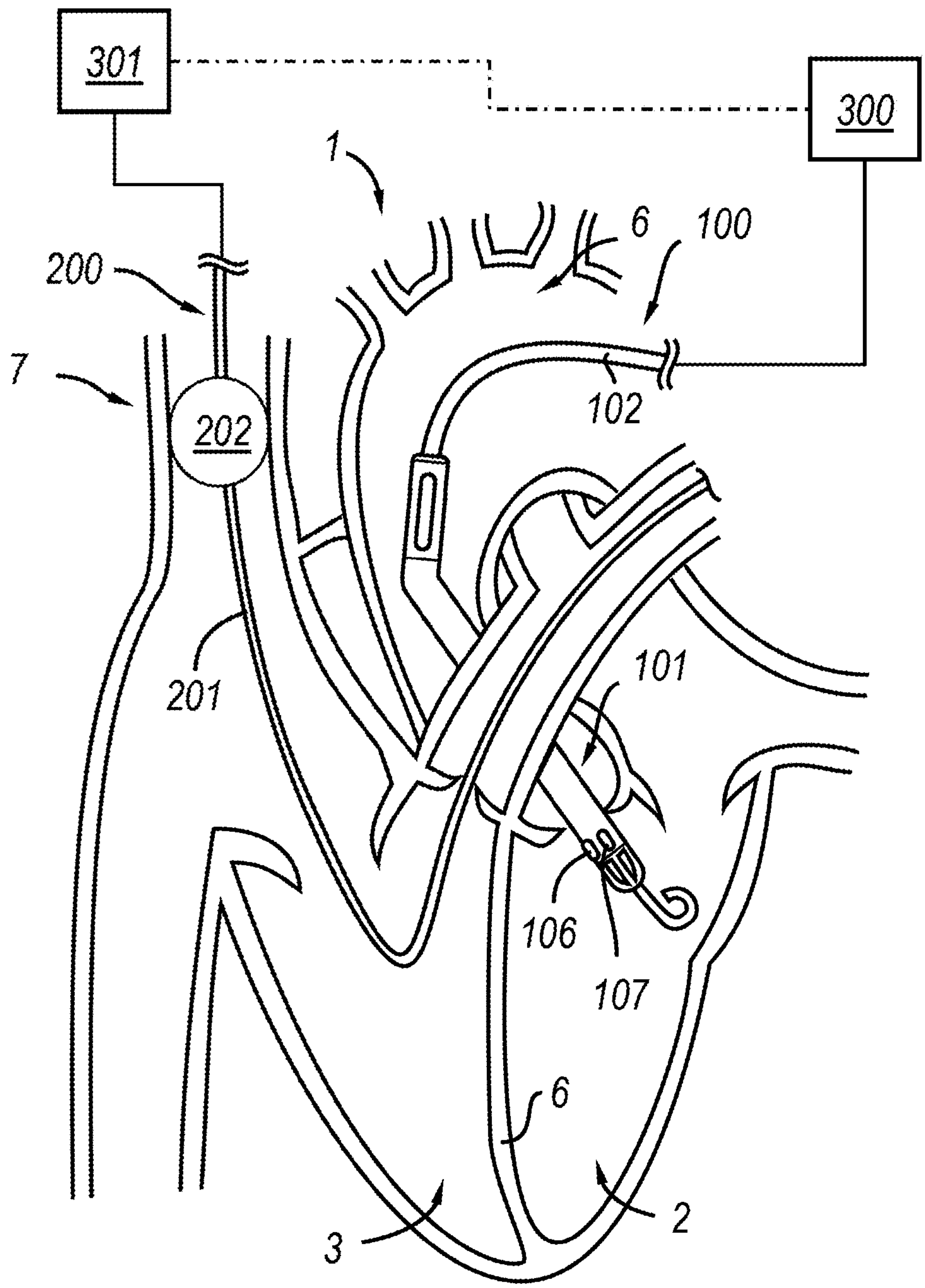
FIG. 3 is an illustration of a heart with two medical devices in place, each device with its own controller.

As shown in FIG. 2, there may be a single controller controlling the VAD and the catheter-based FRE device. As shown in FIG. 3, there may be multiple controllers (300, 301). In some embodiments, the controllers may consist of a single controller. For example, one controller (300) may be operably coupled to the VAD (100), while a second controller (301) may be operably coupled to the catheter-based device (200). The controllers may operably communicate with each other, e.g., via a wired or wireless connection such that the VAD and catheter-based FRE device may be holistically controlled to manage preload and/or septal-shifts, for example.

The controller(s) may be configured to receive information from the VAD (100) and/or the catheter-based FRE device (200). For example, the VAD may include one or more sensors or transducers (e.g., first transducer (106), second transducer (107), etc.) (see FIGS. 2 and 3), and/or the catheter-based FRE device may include one or more sensors or transducers (205, 206) (see FIG. 2).

The term "controller" as used herein may refer to, be part of, or include the following: an Application Specific Integrated Circuit (ASIC); digital, analog, or mixed analog/digital discrete circuits; digital, analog, or mixed analog/digital integrated circuits; a combinational logic circuit; a Field Programmable Gate Array (FPGA); processor circuitry (shared, dedicated, or combined) to execute code; memory circuitry (shared, dedicated, or combined) that stores code executed by the processor circuitry; other suitable hardware components that provide the described functionality; or a combination of some or all of the above, such as in a system on a chip.

The controller may include one or more interface circuits. In some examples, the interface circuit may include a wired or wireless interface to a Local Area Network (LAN), the internet, a Wide Area Network (WAN), or a combination thereof. The functionality of any given controller of the present invention may be distributed among multiple controllers connected via interface circuits. For example, multiple controllers may allow load balancing. In a further example, a server (also referred to as remote, or cloud) controller may perform certain functions on behalf of a client controller.

The controller may include one or more displays, and may include one or more buttons and/or switches. The controller may include memory, and may include one or more non-transitory computer-readable storage media that contain instructions that, when executed, cause the controller to perform various steps.

In some embodiments, the one or more sensors or transducers may include a pressure sensor or an ultrasound transducer. In some embodiments, at least one pressure sensor may be present in a first chamber of the heart (e.g., the left ventricle), and at least one pressure sensor may be present in a second chamber of the heart (e.g., the right ventricle). In some embodiments, only a single pressure sensor may be present. The pressure sensor(s) may be, e.g., optical or electrical sensors. In some embodiments, the catheter-based FRE device also may include at least one pressure sensor. In some embodiments, the VAD may include at least one pressure sensor. In some embodiments, the catheter-based FRE device and the VAD each may include at least one pressure sensor. In some embodiments, the pressure sensor may be configured to determine a pressure of a chamber of the heart in which the sensor is present.

Although described as being a pressure sensor, it will be appreciated that other suitable sensors may be used. For example, in some embodiments, the sensor(s) may include a transducer, such as an ultrasound transducer. Other sensors also may be used in other embodiments as appropriate.

In some embodiments, a sensor or transducer (106, 206) may be present that can determine a distance (207, 208) (e.g., a distance from a sensor to the intraventricular septum). In some embodiments, such a distance sensor or transducer may be present on the catheter-based FRE device. In some embodiments, such a distance sensor or transducer may be present on the VAD. In some embodiments, such distance sensor(s) or transducer(s) may be present on both the catheter-based FRE device and the VAD.

In some embodiments, the sensors or transducers are configured to send information to the controllers.

In some embodiments, the information may include a performance characteristic of the VAD and/or the catheter-based FRE device.

Referring to FIG. 3, such systems can also be used holistically to therapeutically reduce cardiac preload. As used herein, the term "cardiac preload" refers to the initial stretching of the cardiac myocytes prior to contraction. When venous return to the heart is increased, the end-diastolic pressure and volume of the ventricles increases, which stretches the sarcomeres, increasing their preload. In contrast, hypovolemia resulting from a loss of blood volume (e.g., hemorrhage) leads to less ventricular filling and therefore shorter sarcomere lengths (reduced preload).

Active unloading of the left ventricle, via controlled use of the VAD, can reduce left ventricle end-diastolic pressure (LVEDP). Restriction of flow (e.g., preventing blood from entering the right ventricle) may reduce the filling pressures of both the right and left ventricle, represented by right atrium pressure (RAP) and the LVEDP. By combining the two approaches, one can reduce wall stress, reduce septal shift, reduce RAP, reduce LVEDP, and improve myocardial structure including valvular coaptations in a safe manner. For example, one may generate undesired safety events (e.g., suction events) by operating the VAD at a high speed while using the FRE to block the flow of all blood into the right atrium and right ventricle from the SVC for an extended period of time. Thus, the system requires communication between the two devices to operate in a safe fashion while reducing preload and/or shifting septal positioning such as to maximize unloading and circulatory support.

In some embodiments, the disclosed techniques may be used to address pulmonary hypertension (e.g., increased blood pressure in the arteries of the lungs). Increased pressure in the blood vessels of the lungs may involve increased back pressure in the right ventricle (RV). Increased back pressure in the RV typically results in the RV being dilated (and therefore, experiencing a septal shift), where the dilation may lead to right heart failure. One can reduce the load on the RV and/or help the RV recover by blocking the SVC, reducing the load on the right atrium (RA) and reducing the amount of blood coming from the RA.

In some embodiments, the controller(s) may receive information from various sensors, and the controller(s) may be configured to determine a left-sided pressure (e.g., a pressure in the left ventricle). The controller may then be configured to auto-titrate support to offload the left (or right) ventricle based on that determined pressure.

Figure 4:
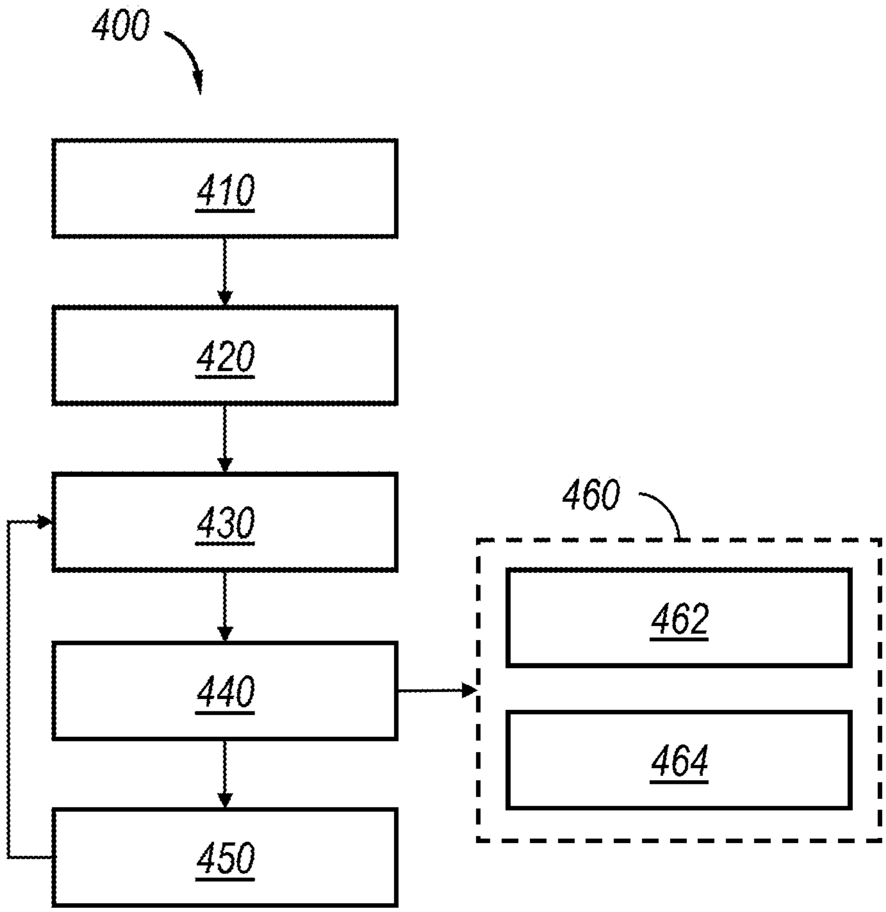
FIG. 4 is a flowchart of a method for therapeutically reducing preloading.

In various aspects, a method for therapeutically reducing preload may be provided. Referring to FIG. 4, the method (400) may include providing (410) a plurality of devices, including a ventricular assist device (VAD) and a catheter-based device comprising an adjustable flow restricting element (FRE) (referred to herein as a "catheter-based FRE device").

The method may include placing (420) the devices in an appropriate location. The VAD may be placed at least partially within either the left or right ventricle of a patient, and the catheter-based FRE device may be placed such that the FRE may be disposed within a superior vena cava (SVC) of the patient.

The method may include receiving (430) information from at least a first device of the plurality of devices.

The information may be from both the VAD and the catheter-based FRE device. In some embodiments, the information may be from the VAD and the at least one performance parameter that is controlled may be of the catheter-based FRE device. In some embodiments, the information may be from the VAD and the at least one performance parameter that is controlled may be of both the VAD and the catheter-based FRE device. In some embodiments, the information may be from the catheter-based FRE device and the at least one performance parameter that is controlled may be of the VAD. In some embodiments, the information may be from the catheter-based device and the at least one performance parameter that is controlled may be of both the VAD and the catheter-based device.

The information may be received by a single controller. The single controller may be configured to control both the VAD and the catheter-based FRE device. In some embodiments, any information from the VAD may be received by a first controller, any information from the catheter-based FRE device may be received by a second controller, and the first controller and second controller may be operably communicating with each other.

The information may include left ventricular end diastolic pressure (LVEDP), right ventricular end diastolic pressure (RVEDP), left atrium pressure (LAP), right atrium pressure (RAP), a differential pressure, left ventricle systolic pressure, right ventricle systolic pressure, an arterial pressure, jugular vein pressure (JVP), motor current, an integrated ECG signal, or a combination thereof.

The information may include a distance, such as a distance from a sensor on one of the devices to a surface of the intraventricular septum.

In some embodiments, the information includes at least one pressure and at least one distance.

In some embodiments, the information includes at least one performance parameter. Such performance parameters may include, e.g., a voltage, a current, a pressure, a resistance, etc., related to the operation of the VAD and/or the catheter-based FRE device.

Although shown and described as receiving information from only one or both of the devices, it will be appreciated that information also may be retrieved from another device (e.g., a wearable patch). In such embodiments, the additional information can be sent to the first and/or second controller and used to monitor and holistically control pre-load.

The method may include determining (440) a first determined value based on the information.

In some embodiments, the determined value may be a pressure. In some embodiments, the determined value may be a maximum, minimum, average, or a function of pressure. In some embodiments, the determined value may be a plurality of pressures. In some embodiments, the determined value may be a change in pressure. In some embodiments, the determined value may be a maximum, minimum, average, or a function of distance. In some embodiments, the determined value may be a change in distance (e.g., a change in maximum, minimum, or average distance).

The method may include controlling (450) at least one performance parameter of at least a second device of the plurality of devices based on the first determined value.

At least one performance parameter may be a rotational speed of a motor of the VAD. In some embodiments, the rotational speed may be increased. In some embodiments, the rotational speed may be decreased. In some embodiments, a limit may be placed on the rotational speed.

At least one performance parameter may be a duty cycle of the FRE. In some embodiments, the duty cycle may be increased. In some embodiments, the duty cycle may be decreased. In some embodiments, the duty cycle may be paused. In some embodiments, the duty cycle may be paused with the flow of blood into the right atrium and right ventricle restricted (i.e., the FRE in an expanded configuration). In some embodiments, the duty cycle may be paused with the flow of blood into the right atrium and right ventricle unrestricted or minimally restricted (i.e., the FRE in a collapsed configuration).

The method may include performing one or more additional steps (460). Such additional steps may include displaying (462) at least one right and left sided hemodynamic metric based on information from the VAD and the catheter-based device. Such additional steps may include determining (464) an unloading status of one or more ventricles.

The method may include automatically iteratively performing the receiving (430), determining (440), and controlling (450) steps of the method to achieve an operational state wherein the unloading status may be a maximally unloaded state that does not compromise patient safety.

Figure 5:
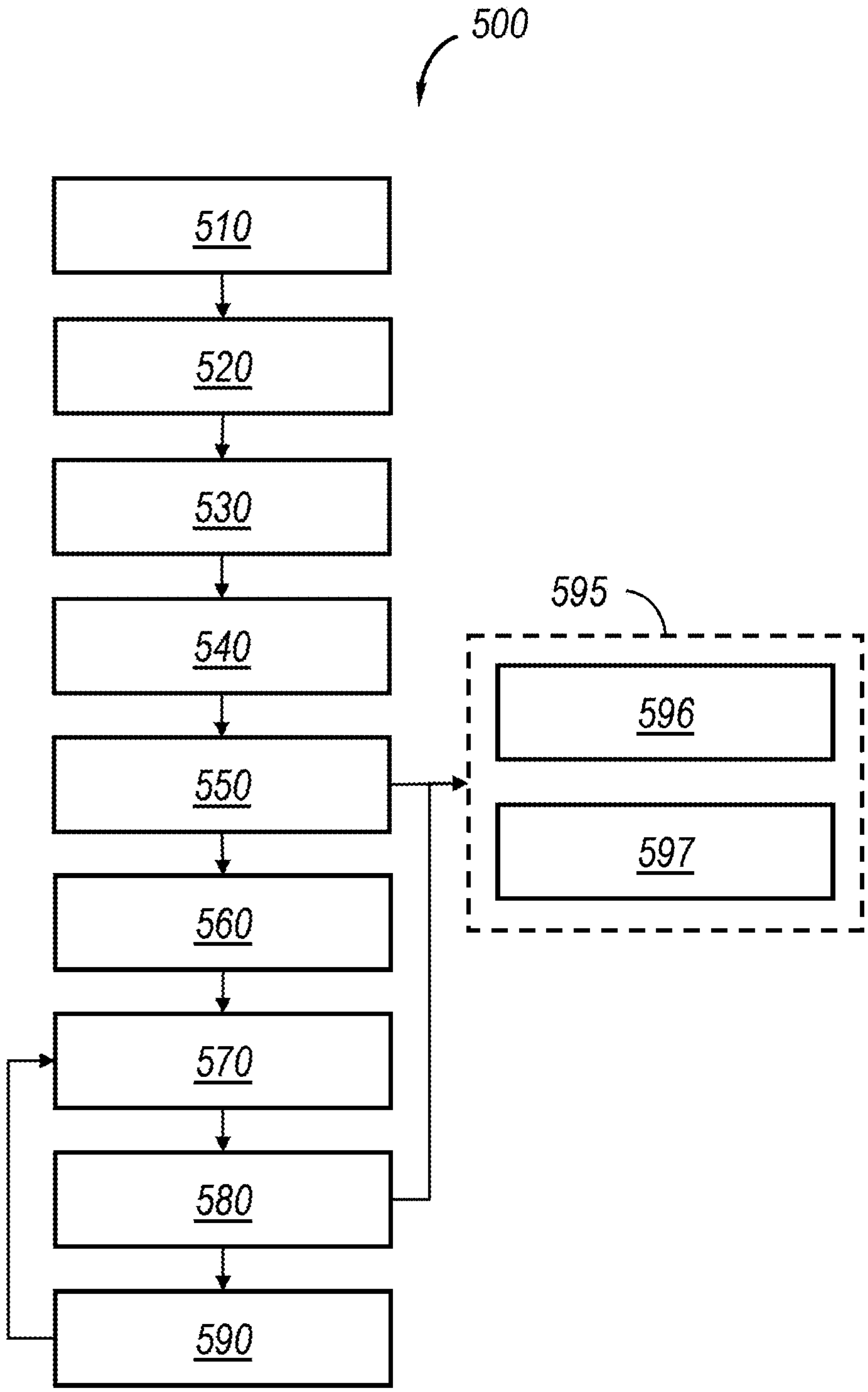
FIG. 5 is a flowchart of a method for modifying the positioning of an intraventricular septum of a patient.

In various aspects, a method for modifying the positioning of an interventricular septum of a patient may be provided. Referring to FIG. 5, the method (500) may include placing (510) a VAD at least partially within either the left or right ventricle of a patient, and placing a catheter-based FRE device comprising an adjustable FRE such that the FRE may be disposed within a superior vena cava (SVC) of the patient.

The method may include receiving (520) first information from the VAD and/or the catheter-based FRE device.

The information may be from both the VAD and the catheter-based FRE device. In some embodiments, the information may be from the VAD and the at least one performance parameter that is controlled may be of the catheter-based device. In some embodiments, the information may be from the VAD and the at least one performance parameter that is controlled may be of both the VAD and the catheter-based FRE device. In some embodiments, the information may be from the catheter-based device and the at least one performance parameter that is controlled may be of the VAD. In some embodiments, the information may be from the catheter-based device and the at least one performance parameter that is controlled may be of both the VAD and the catheter-based device. In some embodiments, the information is from a non-catheter-based device and the at least one performance parameter that is controlled may be of the VAD, the catheter-based FRE device, or both.

The information may be received by a single controller. The single controller may be configured to control both the VAD and the catheter-based FRE device. In some embodiments, any information from the VAD may be received by a first controller, any information from the catheter-based device may be received by a second controller, and the first controller and second controller may be operably communicating with each other.

The information may include left ventricular end diastolic pressure (LVEDP), right ventricular end diastolic pressure (RVEDP), left atrium pressure (LAP), right atrium pressure (RAP), a differential pressure, left ventricle systolic pressure, right ventricle systolic pressure, an arterial pressure, jugular vein pressure (JVP), motor current, an integrated ECG signal, or a combination thereof.

The information may include a distance, such as a distance from a sensor or a transducer on one of the devices to a surface of the interventricular septum. The first information may be a value representative of a pressure, a distance, or both. The distance may be a distance between a sensor or a transducer on the VAD or the catheter-based FRE device and at least a portion of the interventricular septum. The pressure may include a pressure in a right-sided cardiac chamber, a pressure in a left-sided cardiac chamber, a pressure in a great vessel of the heart, or a combination thereof. In some embodiments, the information includes at least one pressure and at least one distance.

In some embodiments, the information includes at least one performance parameter. Such performance parameters may include, e.g., a voltage, a current, a pressure, a resistance, etc., related to the operation of the VAD and/or the catheter-based device.

The method may include determining (530) a first value representative of a first positioning of the interventricular septum based on the first information. For example, based on a difference between a measured pressure differential between the left and right ventricle, and the pressure differential in such chambers when the septum is in a no- or low-stress condition, it is possible to estimate the positioning of the septum.

In some embodiments, the first value may be a quantitative relative value (such as distance relative to an outer wall of the heart, or distance relative to a predetermined target value). In some embodiments, the first value may be a subjective value or classification. For example, the value could be "0" for "no or low" stress on the septum, "±1" for a "moderate" amount of stress in one direction or the other (e.g., positive values for the septum being shifted to the right, negative values for the septum being shifting to the left), and "±2" for "high" stress.

The method may include receiving (540) second information from the VAD and/or the catheter-based device. The method may include determining (550) a second value representative of a second positioning of the intraventricular septum based on the second information.

The method may include adjusting (560) at least one performance parameter of the VAD and/or the catheter-based FRE device based on a difference between the first value and the second value, or if the second value exceeds a predetermined threshold.

The at least one performance parameter may be a rotational speed of a motor of the VAD. In some embodiments, the rotational speed may be increased. In some embodiments, the rotational speed may be decreased. In some embodiments, a limit may be placed on the rotational speed.

The at least one performance parameter may be a duty cycle of the FRE. In some embodiments, the duty cycle may be increased. In some embodiments, the duty cycle may be decreased. In some embodiments, the duty cycle may be paused.

In some embodiments, any adjustment to the VAD may be based at least partially on information received from the catheter-based device. In some embodiments, any adjustment to the catheter-based FRE device may be based on information received from the VAD.

For example, in some embodiments, to shift the septum to the left (i.e., to cause the volume of the left ventricle to become smaller), the system may cause the FRE to change to a collapsed configuration or to alter the duty cycle to have a longer period of time in the collapsed configuration, allowing more blood to flow into the right atrium and right ventricle. The system may also, or alternatively, reduce the rotation speed of the VAD (i.e., reducing the flow rate of blood out of the left ventricle). Based on information the controllers have received, the system may set a lower limit on the rotational speed of the VAD, so that future speed adjustments cannot go below the lower limit, or may set an upper limit on the rotational speed of the VAD, so that future speed adjustments will not allow the VAD to go above the upper limit. These limits may remain in place until, e.g., the controllers receive information indicating it is safe to remove the limits.

In some embodiments, to shift the septum to the right (i.e., to cause the volume of the right ventricle to become smaller), the system may cause the FRE to change to an expanded configuration or to alter the duty cycle to have a longer period of time in the expanded configuration, allowing less blood to flow into the right atrium and right ventricle. The system may also, or alternatively, increase the rotation speed of the VAD (i.e., increasing the flow rate of blood out of the left ventricle). Based on information the controllers have received, the system may set a lower limit on the rotational speed of the VAD, so that future speed adjustments cannot go below the lower limit, or may set an upper limit on the rotational speed of the VAD, so that future speed adjustments will not allow the VAD to go above the upper limit. These limits may remain in place until, e.g., the controllers receive information indicating it is safe to remove the limits.

The method may include performing one or more additional steps (595). Such additional steps may include displaying (596) at least one right and left sided hemodynamic metric based on information from the VAD and the catheter-based device. Such additional steps may include determining (597) an unloading status of one or more ventricles.

The method may also include automatically iteratively performing several steps. Such steps may include receiving (570) third information from the VAD and/or the catheter-based device. The steps may include determining (580) a third value representative of a third positioning of the interventricular septum based on the third information. The method may include adjusting (590) at least one performance parameter of the VAD and/or the catheter-based device based on a difference between the third value and one or more previously determined values, or if the third value exceeds a predetermined threshold.

Various modifications may be made to the systems, methods, apparatus, mechanisms, techniques and portions thereof described herein with respect to the various figures, such modifications being contemplated as being within the scope of the invention. For example, while a specific order of steps or arrangement of functional elements is presented in the various embodiments described herein, various other orders/arrangements of steps or functional elements may be utilized within the context of the various embodiments. Further, while modifications to embodiments may be discussed individually, various embodiments may use multiple modifications contemporaneously or in sequence, compound modifications and the like.

Although various embodiments which incorporate the teachings of the present invention have been shown and described in detail herein, those skilled in the art can readily devise many other varied embodiments that still incorporate these teachings. Thus, while the foregoing is directed to various embodiments of the present invention, other and further embodiments of the invention may be devised without departing from the basic scope thereof.

What is claimed is:

1. A method for providing a therapeutic treatment to reduce preload, the method comprising:

providing a plurality of devices, including a ventricular assist device (VAD) and a catheter-based flow restricting element (FRE) device comprising an adjustable FRE;

placing the VAD at least partially within either a left or right ventricle of a patient, and placing the catheter-based FRE device such that the FRE is disposed within a superior vena cava (SVC) of the patient;

receiving information from at least a first device of the plurality of devices;

determining a first determined value based on the information; and controlling at least one performance parameter of at least a second device of the plurality of devices based on the first determined value, wherein the at least one performance parameter is a rotational speed of a motor of the VAD.

2. The method according to claim 1, wherein the information is from both the VAD and the catheter-based FRE device.

3. The method according to claim 1, wherein the information is from the VAD and the at least one performance parameter that is controlled is of the catheter-based FRE device.

4. The method according to claim 1, wherein the information is from the VAD and the at least one performance parameter that is controlled is of both the VAD and the catheter-based FRE device.

5. The method according to claim 1, wherein the information is from the catheter-based FRE device and the at least one performance parameter that is controlled is of the VAD.

6. The method according to claim 1, wherein the information is from the catheter-based FRE device and the at least one performance parameter that is controlled is of both the VAD and the catheter-based device.

7. The method according to claim 1, wherein the information is received by a single controller.

8. The method according to claim 7, wherein the single controller is configured to control both the VAD and the catheter-based FRE device.

9. The method according to claim 1, wherein any information from the VAD is received by a first controller, any information from the catheter-based device is received by a second controller, and the first controller and second controller are operably communicating with each other.

10. The method according to claim 1, wherein the information is from a non-catheter-based device and the at least one performance parameter that is controlled is of the VAD, the catheter-based FRE device, or both.

11. The method according to claim 1, wherein the information includes left ventricular end diastolic pressure (LVEDP), right ventricular end diastolic pressure (RVEDP), left atrium pressure (LAP), right atrium pressure (RAP), a differential pressure, left ventricle systolic pressure, right ventricle systolic pressure, an arterial pressure, jugular vein pressure (JVP), motor current, an integrated ECG signal, or a combination thereof.

12. The method according to claim 1, wherein the rotational speed is increased.

13. The method according to claim 1, wherein the rotational speed is decreased.

14. The method according to claim 1, wherein a limit is placed on the rotational speed.

15. The method according to claim 1, further comprising displaying at least one right and left sided hemodynamic metric based on information from the VAD and the catheter-based FRE device.

16. The method according to claim 1, further comprising determining an unloading status of one or more ventricles.

17. The method according to claim 16, further comprising automatically iteratively performing the receiving, determining, and controlling steps to achieve an operational state wherein the unloading status is a maximally unloaded state that does not compromise patient safety.

18. A method for modifying positioning or curvature of an interventricular septum of a patient, the method comprising:

placing a ventricular assist device (VAD) at least partially within either a left or right ventricle of a patient, and placing a catheter-based device comprising a flow restricting element (FRE) (catheter-based FRE device)

such that the FRE is disposed within a superior vena cava (SVC) of the patient, the FRE being adjustable;

receiving first information from the VAD and/or the catheter-based FRE device;

determining a first value representative of a first positioning or curvature of the interventricular septum based on the first information;

receiving second information from the VAD and/or the catheter-based FRE device;

determining a second value representative of a second positioning or curvature of the interventricular septum based on the second information; and adjusting at least one performance parameter of the VAD and/or the catheter-based FRE device based on a difference between the first value and the second value, or if the second value exceeds a predetermined threshold.

19. A system for providing a therapeutic treatment to reduce preload, comprising:

a plurality of devices, including:

a ventricular assist device (VAD) configured to be disposed at least partially in either left or right ventricle; and a catheter-based device comprising a flow restricting element (FRE) (catheter-based FRE device), the FRE configured to be disposed within a superior vena cava (SVC) of a patient; and one or more controllers, each controller comprising one or more processors and a non-transitory computer-readable storage media containing instructions that, when executed by the controller, causes the one or more controllers to, individually or in combination:

receive information from at least a first device of the plurality of devices;

determine a first determined value based on the information; and control at least one performance parameter of at least a second device of the plurality of devices based on the first determined value, wherein the at least one performance parameter is a rotational speed of a motor of the VAD.

* * * * *